United States Patent [19]

Gosteli

[11] 4,020,098

[45] Apr. 26, 1977

[54] PROCESS FOR THE PREPARATION OF 5-SUBSTITUTED RESORCINOLS AND RELATED INTERMEDIATES

[75] Inventor: Jacques Gosteli, Basel, Switzerland

[73] Assignee: Ciba-Geigy Corporation, Ardsley, N.Y.

[22] Filed: July 9, 1975

[21] Appl. No.: 594,412

Related U.S. Application Data

[62] Division of Ser. No. 419,579, Nov. 28, 1973, abandoned.

[30] Foreign Application Priority Data

Dec. 7, 1972  Switzerland ............... 17825/72

[52] U.S. Cl. ..................... 260/473 S; 260/625
[51] Int. Cl.$^2$ ........................... C07C 69/76
[58] Field of Search .................. 260/473 S

[56] References Cited
FOREIGN PATENTS OR APPLICATIONS 670,676  1/1966  Belgium .................. 260/473

OTHER PUBLICATIONS

Mechoulam, et al., J. Chem. Soc. D. 1969, (7), 343-3 (Eng), (Chemical Abst.).

Primary Examiner—Paul J. Killos
Attorney, Agent, or Firm—Joseph G. Kolodny; Maitner John J.; Groeger Theodore O.

[57] ABSTRACT

According to the present invention, 5-substituted resorcinols of the formula I

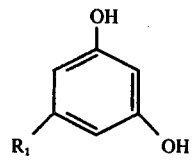

(I)

wherein $R_1$ represents a hydrocarbon radical, optionally unsubstituted or substituted by inert substituents, are prepared by reacting a carboxylic acid ester of the formula II $$R_1 - C \quad C - CO - O - R_2 \quad (II)$$

wherein $R_2$ represents a non-aromatically bound lower hydrocarbon radical, in the presence of an alkaline condensation agent, with a diester of 3-oxoglutaric acid of the formula III $$R_3-O-CO-CH_2-CO-CH_2-CO-O-R_4 \quad (III)$$

wherein $R_3$ and $R_4$ represent non-aromatically bound lower hydrocarbon radicals; hydrolyzing the resulting dihydroxyisophthalic acid acid ester of the formula IV

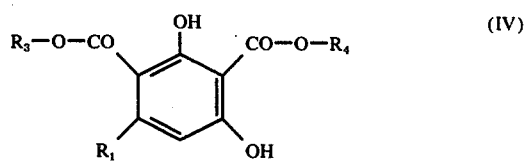

(IV)

and decarboxylating the hydrolyzed product, a specific embodiment is the preparation of 5-pentylresorcinol.

9 Claims, No Drawings

PROCESS FOR THE PREPARATION OF 5-SUBSTITUTED RESORCINOLS AND RELATED INTERMEDIATES

This is a division of application Ser. No. 419,579, filed Nov. 28, 1972, now abandoned.

The present application relates to a new, technically advantageous process for the preparation of 5-substituted resorcinols and related intermediates.

5-Substituted resorcinols, particularly 5-alkylresorcinols, are of considerable scientific as well as commerical interest, since, on the one hand, some representatives of this class of substances occur naturally and, in some cases, are usable moreover as starting materials for the preparation of further important natural substances, and, on the other hand, some of these substances have antimicrobial properties. [cp. e.g. J. Pharm. Soc. Japan 68, 303–305 (1951)] The processes and reaction sequences known for preparation of homologues of orcinol and further 5-substituted resorcinols can be roughly divided into those in which the starting materials are aromatic substances, especially derivatives of 3,5-dihydroxybenzoic acid or diethers of 3,5-dihydroxybenzaldehyde, and those in which the ring is formed of non-cyclic starting materials. Of the last-mentioned reaction sequences, the one probably most generally applicable has 3-substituted acrylic acid esters as starting materials, which are firstly reacted with the sodium compound of the acetoacetic acid ethyl ester to the corresponding 6-substituted 2,4-dioxocyclohexane-1-carboxylic acid ethyl esters. Bromination of these with bromine in glacial acetic acid to give the corresponding 6-substituted 3,5-dibromo-2,4-dioxyocyclohexane-1-carboxylic acid alkyl esters and debromination with catalytically activated hydrogen, e.g. in the presence of a palladium charcoal catalyst, yield aromatic analogues, the 2,4-dihydroxybenzoic acid ethyl esters correspondingly substituted in the 6-position, from which, finally, the corresponding 5-substituted resorcinols are obtained by alkaline hydrolysis, liberation of the acids and heating. This reaction sequence has been used, for example, by R. M. Anker and A. H. Cook, J. Chem. Soc., 311 (1945), as well as by F. Korte and H. Seiper, Justus Liebigs Ann. Chem. 630, 71 (1960), for the preparation of olivetol (5-pentyl-resorcinol). R. M. Anker and A. H. Cook (loc. cit.) concerned themselves also with a reaction sequence in which the conversion of a dioxocyclohexane derivative into a dihydroxybenzene derivative is eliminated; namely, the reaction sequence comprising the reaction of (1-alkynyl)-methyl ketones with sodium malonic acid diethyl ester to 4-alkyl-6-methyl-2-oxo-2H-pyrane-3-carboxylic acid ethyl esters, followed by rearrangement and decarbethoxylation thereof to give the corresponding 5-alkyl-resorcinols by heating with potassium hydroxide. However, on account of the fact that the required alkynyl methyl ketone is not readily available, the authors abandoned this essentially possible mode of preparation for olivetol. T. Kato and T. Hozumi, Chem. Pharm. Bull. 20, 1574–1578 (1972) reacted acetoacetic acid ethyl ester with diketene in the presence of sodium hydride in tetrahydrofuran to obtain, likewise directly, an aromatic compound, the 2,4-dihydroxy-6-methyl-benzoic acid ethyl ester, which is easily convertible into orcinol; there resulted, however, a second reaction product, 2,6-dimethyl-4-oxo-4H-pyrane-3-carboxylic acid ethyl ester. It was possible also to react other acylacetic acid esters in an analogous manner, particularly alkanoylacetic acid ester, such as, e.g. hexanoylacetic acid ethyl ester, with diketene. From the initially formed 6-substituted 2,4-dihydroxybenzoic acid esters, such as, e.g. 6-pentyl-2,4-dihydroxybenzoic acid ethyl ester, the corresponding 5-substituted resorcinols, such as, e.g. olivetol, could then be readily obtained by alkaline hydrolysis and heating of the liberated acids. However, the reduced yield owing to the simultaneous formation of pyrone and the fact that the acylacetic acid esters, especially the alkanoylacetic acid esters, with exception of the acetoacetic acid ester are not readily available are factors adversely affecting the practical importance of the aforementioned process, at least with regard to its application for the preparation of homologues and analogues of orcinol.

It has now been found that 5-substituted resorcinols of the general formula I

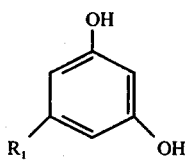

(I)

wherein

R₁ represents a hydrocarbon radical optionally containing inert substituents, and related intermediates can be prepared in a simple and technically advantageous manner by a process in which a carboxylic acid ester of the general formula II

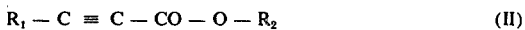

$R_1 - C \equiv C - CO - O - R_2$ (II)

wherein

R₂ represents a non-aromatically bound lower hydrocarbon radical, and R₁ has the meaning given under formula I, is reacted, in the presence of an alkaline condensation agent, with a diester of 3-oxoglutaric acid of the general formula III

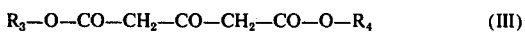

$R_3-O-CO-CH_2-CO-CH_2-CO-O-R_4$ (III)

wherein

R₃ and R₄ represent non-aromatically bound lower hydrocarbon radicals;

and, optionally, the dihydroxyisophthalic acid ester of the general formula IV

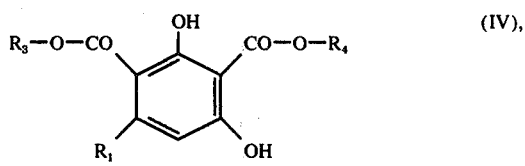

(IV), wherein R₁ has the meaning given under formula I and R₃ and R₄ have the meaning given under formula II, separated from the resulting crude product; or the resulting crude product, or a compound separated from this of the general formula IV, hydrolysed, and, in the same operation and/or subsequently, decarboxylated.

The hydrocarbon radical R₁ optionally containing inert substituents contains, including these substituents, at most 21 carbon atoms. Inert substituents present can be, for example, alkoxy having 1 to 4 carbon atoms, and on aromatic rings also halogen, preferably chlorine or fluorine, or alkyl having 1 to 4 carbon atoms. For example, $R_1$ is the methyl group, particularly however an aliphatic hydrocarbon radical, or a saturated aliphatic hydrocarbon radical, substituted by lower alkoxy, having in all 2-21 carbon atoms, especially a corresponding alkyl group having 2 to 21, and preferably 3 to 12, carbon atoms, such as the ethyl, propyl, isopropyl, butyl, tert.butyl, 1,1-dimethylpropyl, hexyl, 1,1-dimethylbutyl, heptyl, 1-methylhexyl, octyl, nonyl, 1,2-dimethylheptyl, decyl, 1,2,2-trimethylheptyl, undecyl, dodecyl, tridecyl, 1-methyltridecyl, pentadecyl, heptadecyl, octadecyl nonadecyl, 1-methylnonadecyl or heneicosyl group and, in particular; the pentyl group, or an alkenyl group having likewise at most 21, and preferably 3 to 12, carbon atoms, such as the 1-propenyl, allyl, 2-methylallyl, 2-butenyl, 3-methyl-2-butenyl, 3-undecenyl, 8-pentadecenyl or 10-pentadecenyl group, or an aromatic hydrocarbon radical containing at most 21, and preferably at most 10, carbon atoms, especially a phenyl radical optionally substituted as mentioned above, e.g. the phenyl, o-, m- or p-chlorophenyl radical, o-, m- or p-fluorophenyl radical, o-, m- or p-anisyl radical, 3,4-dimethoxyphenyl, p-ethoxyphenyl, p-isopropoxyphenyl, p-butoxyphenyl, o-, m- or p-tolyl radical, p-ethylphenyl, p-propylphenyl or p-isopropylphenyl, p-tert.butylphenyl radical, or an aliphatic hydrocarbon radical unsubstituted or preferably substituted on the aromatic ring by halogen, particularly chlorine or fluorine, alkyl or alkoxy each having 1 to 4 carbon atoms, and containing at most 21, and preferably at most 12, carbon atoms, for example, a correspondingly substituted phenylalkyl radical having 1 to 4 carbon atoms in the alkyl moiety, such as the benzyl, p-chlorobenzyl, p-fluorobenzyl, p-methylbenzyl, p-isopropylbenzyl, o-, m- or p-methoxybenzyl, 3,4-dimethoxybenzyl, p-ethoxybenzyl, p-isopropoxybenzyl, p-butoxybenzyl, phenethyl, p-chlorophenyl, p-fluorophenylethyl, p-methylphenethyl, p-isopropylphenethyl, p-methoxyphenethyl, 3,4-dimethoxyphenethyl, p-butoxyphenethyl, 3-phenylpropyl or 4-phenylbutyl radical, or an optionally correspondingly substituted styrene or cinnamyl radical, such as, e.g. the p-chlorostyrene, p-fluorostyrene, p-isopropylstyrene, p-methoxystyrene, 3,4-dimethoxystyrene, cinnamyl, p-chlorocinnamyl, p-fluorocinnamyl, p-methylcinnamyl or p-methoxycinnamyl radical. As a saturated aliphatic hydrocarbon radical substituted by alkoxy having 1 to 4 carbon atoms, $R_1$ likewise contains up to 21, preferably however 2 to 7, carbon atoms, and is, e.g. a methoxymethyl, ethoxymethyl, propoxymethyl, butoxymethyl, 2-methoxyethyl, 2-ethoxyethyl, 2-propoxyethyl, 2-isopropoxyethyl, 2-butoxyethyl, 3-methoxypropyl, 3-ethoxypropyl, 3-isopropoxypropyl or 3-butoxypropyl group. Furthermore, $R_1$ is, e.g. a cycloaliphatic hydrocarbon radical having at most 21, and preferably 3 to 10, carbon atoms, such as a cycloalkyl or cycloalkylalkyl radical having 3 to 7 ring members, optionally alkyl-substituted on the ring, e.g. a cyclopropyl, cyclobutyl, cyclopropylmethyl, cyclobutylmethyl, cyclopentyl, 2-cyclopropylethyl, cyclohexyl, cyclopentylmethyl, 4-methylcyclohexyl, cycloheptyl, 3,4-dimethylcyclohexyl, 4-methylcycloheptyl, 2-cyclohexylethyl, 4-isopropylcyclohexyl or 4-isopropylcyclohexylmethyl group.

The non-aromatically bound lower hydrocarbon radicals $R_2$ of the starting materials of the general formula II preferably contain 1 to 7 carbon atoms and are, for example, cyclohexyl or benzyl groups, preferably, however, alkyl groups having 1 to 4 carbon atoms, such as isopropyl or tert.butyl groups, and especially methyl or ethyl groups. The same groups are also suitable as hydrocarbon radicals $R_3$ and $R_4$ of the starting materials of the general formula III and of the intermediates of the general formula IV; particularly preferred in this case are methyl groups.

The intermediates of the general formula IV can also be used as starting materials for other syntheses. Of special importance are the intermediates of the general formula IVa

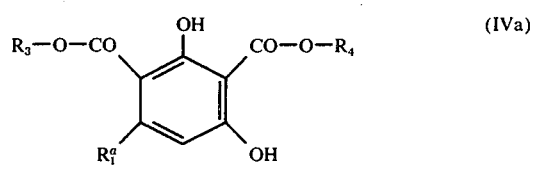

wherein
$R_1^a$ represents an aliphatic hydrocarbon radical having 2 to 21 carbon atoms, particularly a corresponding alkyl group, or a phenyl radical unsubstituted, or substituted by halogen, alkyl or alkoxy each having 1 to 4 carbon atoms,
and $R_3$ and $R_4$ have the meaning given under formula I, especially, however, alkyl groups having 1 to 4 carbon atoms, specially ethyl groups and, in particular, methyl groups. Consequently, the carrying out of the first and, optionally, of the further steps of the reaction sequence according to the invention by a process in which the starting materials are compounds of the general formula I wherein $R_1$ corresponds to the aforementioned narrower definition of $R_1^a$ constitutes a preferred embodiment of the process according to the invention.

Suitable alkaline condensation agents and solvents for the first step of the above defined reaction sequence are, for example, alkali metal hydrides, particularly sodium hydride, in inert organic solvents, such as, e.g. benzene, toluene or 1,2-dimethoxyethane, as well as alkali metal alkanolates, especially sodium or potassium ethylate or -tert.butylate in the corresponding alkanols, particularly abs. ethanol or tert.butanol.

Preferably, the starting materials of the general formulae II and III are employed in approximately equimolar amounts, and the alkaline condensation agent, with respect to this, in an approximately double-molar to ca. 2.5-fold molar amount. The alkaline condensation agent is added, however, in portions or in addition sequences, whereby various temperatures are maintained. Firstly, the approximately equimolar amount is added in the cold state, i.e. preferably at 0° C to room temperature. After ca. 15–90 minutes reaction time, the ca. 1- to 1.5-fold molar amount is added with a gradual increase of temperature, and the reaction mixture then heated, if necessary in a closed vessel, for a further ca. 0.5 – 5 hours to temperatures of between ca. 80° C and 140° C, in order to complete the intramolecular ester condensation. The resulting crude products contain, besides the compounds of the general formula IV, in most cases already a certain proportion of decarbalkoxylation products and possibly also a small amount of final product of the general formula I. It is advantageous, therefore, that the crude products by used direct for the optionally following next steps, hydrolysis and optionally simultaneous decarboxylation;

for these steps, however, the previously separated compounds of the general formula IV can also be used.

Hydrolysis of the crude products containing the compounds of the general formula IV or of the separated compounds of the general formula IV can be performed in alkaline medium or, with simultaneous decarboxylation, also in acid medium. Suitable as an alkaline medium are, for example, diluted, aqueous or aqueous-organic alkali hydroxide solutions, e.g. aqueous-alkanolic alkali hydroxide solutions, particularly ca. 0.5N to 2N aqueous sodium or potassium hydroxide solutions. The alkaline hydrolysis is preferably performed at elevated temperature, e.g. at a temperature of between 60° C and 100° C, especially at the boiling temperature of the reaction mixture, the reaction time being ca. 0.5 to 5 hours.

The acid hydrolysis can be effected, for example, by heating a compound of the general formula IV or a crude product containing a compound of the general formula IV in aqueous sulphuric acid, as well as in concentrated or dilute hydrochloric acid, preferably at a temperature of between ca. 50° C and the boiling temperature of the acid medium. If simultaneous decarboxylation is to occur, then it is preferable to use sulphuric acid having a lower water content, e.g. with a mixture ratio of conc. sulphuric acid to water of 10 to 1 to 1 to 4 parts by volume, and to boil the reaction mixture for ca. 1 to 20 hours, or until the evolution of carbon dioxide ceases.

The decarboxylation step subsequent to an alkaline hydrolysis or to a mild acid hydrolysis is carried out, e.g. by heating the liberated dicarboxylic acids, or preferably the crude products of hydrolysis which already contain, besides the dicarboxylic acid, corresponding monocarboxylic acids as well as some final product of the general formula I, in the presence or absence of higher-boiling organic solvents or diluents, such as, e.g. 1,2,3,4-tetrahydronaphthalene, to a temperature of between 150° C and 250° C, or preferably in aqueous sulphuric acid, under the reaction conditions previously given for acid hydrolysis and simultaneous decarboxylation, for ca. 1–20 hours, or until the evolution of carbon dioxide ceases.

The invention also concerns those modifications of the process whereby a compound occurring as an intermediate at some stage of the process is taken as the starting material and the uncompleted steps of the process are performed, or whereby the process is interrupted at some stage, or whereby a starting material is formed under the reaction conditions, or whereby a starting material of the general formula II is used which, by virtue of the structure of the radical $R_1$, exists as a racemate or as an isolated optical antipode or, in the case of diastereometic compounds, as a specific racemate or likewise as an isolated optical antipode.

Some representatives of the starting materials of the general formula II are known. The 1-octinic acid methyl ester usable for the preparation of olivetol has been produced on a commercial scale for a long time on account of its odoriferous properties. Further starting materials of the general formula II can be prepared in a manner analogous to that in which the known compounds are obtained. They can be prepared, for example, by reaction of the sodium compounds or of other metal compounds of acetylenes substituted by the radical $R_1$ with chloroformic acid esters of which the alcohol component corresponds to the radical $R_2$. There are some representatives known also of starting materials of the general formula III, which are more frequently designated as acetonedicarboxylic acid esters; the dimethyl ester is particularly readily available.

Compared with known processes for preparation of the same substances, the process comprising the reaction sequence according to the invention has the particular advantage that aromatic compounds are obtained direct with cyclisation, and that hence the conversion of dioxocycloalkane derivatives into dihydroxybenzene derivatives can be avoided without accompanying disadvantages having to be accepted, such as the necessity of rearrangement of initially formed pyrone derivatives, and/or resulting low yields, as well as the relatively great difficulty of obtaining the starting materials, especially those for the particularly interesting orcinol homologues having an alkyl group containing at least two, preferably at least 5, carbon atoms. Particularly favourable for the above mentioned reasons is, on the other hand, the situation with regard to the starting materials for the synthesis of olivetol.

The following examples further illustrate the carrying out of the process according to the invention for the preparation of compounds of the general formula I; the examples, however, are not intended in any way to limit the scope of the invention. The temperature values are expressed in degrees Centigrade.

EXAMPLE 1 a. An amount of 9.6 g (0.20 mole) of sodium hydride (50% oil suspension) is added portionwise in a nitrogen atmosphere, with stirring and ice cooling (internal temperature: 10°) to the mixture of 34.8 g (0.20 mole) of 3-oxoglutaric acid dimethyl ester and 30.8 g (0.20 mole) of 2-octinic acid methyl ester in 500 ml of abs. benzene. The ice bath is removed, and the yellowish solution stirred for a further 15 minutes at room temperature before the second portion of 11.2 g (0.23 mole) of sodium hydride is added without cooling. The reaction mixture is refluxed for one hour and the resulting yellow suspension poured, after cooling, on ca. 600 g of ice. The aqueous phase is separated, and washed with 500 ml of ether; the ether solution is combined with the organic phase and the whole extracted twice with 200 ml of 0.2N sodium hydroxide solution each time. The alkaline solution is combined with the aqueous phase, the whole filtered through purified diatomaceous earth and acidified with conc. hydrochloric acid. After cooling, the colourless emulsion is extracted with 500 ml of ether, the extract dried over magnesium sulphate and concentrated by evaporation. After drying in vacuo, there remains an amount of 47.3 g of crude product in the form of a yellow crystallising oil. This is then dissolved in 50 ml of isopropanol and forthwith the 2,4-dihydroxy-6-pentylisophthalic acid dimethyl ester commences to precipitate in the form of large needles. After a standing time of ca. 14 hours in a refrigerator, the crystals are filtered off under suction, washed with a little cold isopropanol and dried: the yield at this stage consists of 33.82 g of 2,4-dihydroxy-6-pentyl-isophthalic acid dimethyl ester as yellowish crystals, M.P. 59°–60°. The mother liquor residue is dissolved in 60 ml of benzene and the solution applied to a silica gel column (80 g). The subtance migrating, on elution with benzene, as a light yellow zone is collected in 2 fractions each of 200 ml. concentration of these fractions in vacuo and crystallisation of the residue from a little isopropanol yield a second portion of, in this case, 4.14 g of reaction product in the form of needles, M.P. 59°–60°; total yield 37.96 g, corresponding to 64% of theory.

(The commercial product used as 2-octinic acid methyl ester contains, according to the gas chromatographical determination, 94% of pure substance. If this content is taken into account, the yield is increased to 68.2% of the theoretical amount.)

b. 83.4 g (0.282 mole) of 2,4-dihydroxy-6-pentylisophthalic acid dimethyl ester is refluxed in 810 ml of 0.67N sodium hydroxide solution for 2 hours under nitrogen. The reaction mixture is cooled, 500 ml of ether added and the whole carefully acidified with 50 ml of conc. hydrochloric acid (carbon dioxide evolution!). The mixture is shaken in a separating funnel, the ether layer separated and the aqueous layer subsequently extracted with 200 ml of ether; the ether solutions are dried over magnesium sulphate and concentrated in vacuo: the resulting yield is 65.2 of crude 2,4-dihydroxy-6-phenyl-isophthalic acid as oil, which already contains decarboxylation products.

c. The crude product obtained according to (b) is stirred with 200 ml of diluted sulphuric acid (volume ratio of conc. sulphuric acid to water = 5:1), until a clear solution is formed. This is allowed to stand for one hour at room temperature; it is then poured into a three-necked flask in which 500 g of ice has been placed, and the formed suspension refluxed for 14 hours in a nitrogen atmosphere. The suspension obtained after cooling is extracted twice with 500 ml of ether each time; the combined ether solutions are extracted four times with 200 ml of 2N sodium hydroxide solution each time, the basic extracts combined, cooled with ice and acidified with 160 ml of conc. hydrochloric acid. The reaction product precipitating in the form of oil is taken up in 500 ml of ether; the solution is washed with water, dried over magnesium sulphate, and concentrated in vacuo to obtain 49.5 g of crude product as reddish oil. Purification is effected by distillation in high vacuum. The olivetol (5-pentylresorcinol) passing over under 0.002 – 0.001 Torr at 126°–130° is obtained firstly as a pale yellow, viscous oil, which fully crystallises on standing, M.P. 48°–50°; yield 45.2 g, 89.3% of the theoretical value.

EXAMPLE 2

1.0 g (0.00338 mole) of 2,4-dihydroxy-6-pentylisophthalic acid dimethyl ester is stirred in 10 ml of a mixture of conc. sulphuric acid and water (volume ratio = 5:1) until a solution is obtained, and this then heated for 4 hours in a bath at 100°. After cooling, the solution is poured on ice and extracted twice with ether (100 ml each time). The combined ethereal layers are extracted with 2 portions of 1N sodium hydroxide solution and the basic extracts acidified with hydrochloric acid; the reaction product precipitating in the form of oil is subsequently taken up in ether. The solution dried with magnesium sulphate yields, after concentration in vacuo, 481 mg of yellowish oil, which crystallises on standing. The yield of crude olivetol amounts to 79% of theory.

EXAMPLE 3 a. 7.90 g (0.1645 mole) of a 50% suspension of sodium hydride in mineral oil is added in a nitrogen atmosphere, with stirring and ice cooling, to the solution of 26.3 g (0.1645 mole) of phenylpropiolic acid methyl ester and 28.6 g (0.1645 mole) of 3-oxoglutaric acid dimethyl ester in 400 ml of abs. benzene. The ice bath is then removed and the reaction mixture stirred for a further 15 minutes. A second portion of 9.20 g (0.1915 mole) of a 50% sodium hydride suspension is added and the reaction mixture refluxed for eight hours. After cooling, it is poured on 1000 ml of ice water; an amount of 500 ml of ether is added and the whole shaken. The ether layer is separated, washed with 250 ml of 0.5N sodium hydroxide solution, and the basic extract combined with the original water phase. The whole is acidified with concentrated hydrochloric acid, and the precipitating oil extracted twice with 300 ml of dichloromethane each time. The organic extract is dried with magnesium sulphate and concentrated in vacuo to thus obtain 42.45 g of crude product in the form of oil, which crystallises on standing.

Purification is effected by recrystallisation from 500 ml of methanol: the yeild from this is 26.45 g of 2,4-dihydroxy-6-phenyl-isophthalic acid dimethyl ester in the form of almost colourless crystals, M.P. 126°–128°.

It is possible to obtain from the concentrated mother liquor a further 2.35 g of pure substance as almost colourless crystals, M.P. 126°–128°; yield 58.1% of theory.

b. 6.00 g (0.0199 mole) of 2,4-dihydroxy-6-phenyl-isophthalic acid dimethyl ester is dissolved under nitrogen in 40 ml of water and 40 ml of 2N sodium hydroxide solution. The light-red solution is refluxed for one hour; it is then cooled with an ice bath and carefully acidified with 8.0 ml of concentrated hydrochloric acid (carbon dioxide evolution). The mixture is then refluxed and boiled for 14 hours in a nitrogen atmosphere. The emulsion obtained after cooling is extracted twice with 100 ml of ether each time. The combined ether layers are dried with magnesium sulphate and concentrated in vacuo to obtain 3.98 g of crude product in the form of yellow crystals. This crude product is dissolved in 20 ml of ether; 50 ml of benzene is added and the ether then distilled off. 5-Phenylresorcinol crystallises out on standing. After cooling, there is added 50 ml of hexane, and the crystals are filtered off under suction; this yields 2.44 g of cream-coloured crystals, M.P. 154°–158°. Repeated crystallistion from 40 ml of benzene with the addition of 40 ml of hexane yields 2.03 g of 5-phenylresorcinol as colourless crystals, M.P. 157° – 158°.

EXAMPLE 4 a. 1.20 g (0.025 mole) of a 50% suspension of sodium hydride in mineral oil is added in a nitrogen atmosphere, with stirring and ice cooling, to the solution of 2.80 g (0.025 mole) of tetrolic acid ethyl ester and 5.05 g (0.025 mole) of 3-oxoglutaric acid diethyl ester in 65 ml of abs. benzene. The ice bath is then removed and the reaction mixture stirred for a further 15 minutes at room temperature. A second portion, this time of 1.34 g (0.028 mole), of the mentioned sodium hydride suspension is added and the reaction mixture refluxed for one hour. After cooling, the mixture is poured on 250 ml of ice water and extracted with 250 ml of ether. The ethereal phase is extracted with 100 ml of 0.5N sodium hydroxide solution, and the basic extract combined with the original aqueous phase. These phases are acidified with concentrated hydrochloric acid, and the precipitating oil extracted twice with 250 ml of ether each time. The combined ethereal extracts are dried over magnesium sulphate, and concentrated in vacuo to obtain 5.72 g of an oil, which crystallises on standing. Chromatography of this crude product on silica gel with benzene as the eluant, combination of the fluorescent eluate fractions and concentration by evaporation yield 4.05 g of 6-methyl-2,4-dihydroxy-isophthalic acid diethyl ester in the form of colourless crystals, M.P. 61° - 62°; yield 60.5% of theory.

b. 1.0 g (0.00373 mole) of 2,4-dihydroxy-6-methylisophthalic acid diethyl ester is stirred, in a manner analogous to that in Example 2, in 10 ml of a mixture of conc. sulphuric acid and water (volume ratio 5:1) until a solution is obtained, and this subsequently heated in a bath at 100° for 4 hours. After processing, the resulting crude product is taken up in water, and the solution treated with active charcoal. Concentration of the filtered solution in vacuo yields orcinol as monohydrate, M.P. 57°–58°.

What I claim is:

1. A compound of the formula IVa $$\text{(IVa)}$$

wherein
$R_1{}^a$ represents alkyl having 3–12 carbon atoms or phenyl, and $R_3$ and $R_4$ each represents lower alkyl.

2. A compound as claimed in claim 1, in which $R_1{}^a$ represents alkyl having 3–12 carbon atoms, and $R_3$ and $R_4$ each represents lower alkyl.

3. A compound as claimed in claim 1, in which $R_1{}^a$ represents pentyl, and $R_3$ and $R_4$ each represents lower alkyl.

4. A compound as claimed in claim 1, in which $R_1{}^a$ represents phenyl, and $R_3$ and $R_4$ each represents lower alkyl.

5. A compound as claimed in claim 1, which is 2,4-Dihydroxy-6-pentyl-isophthalic acid dimethyl ester.

6. A compound as claimed in claim 1, which is 2,4-Dihydroxy-6-phenyl-isophthalic acid dimethyl ester.

7. Process for the preparation of dihydroxyisophthalic acid esters of the formula IV $$\text{(IV)}$$

wherein
$R_1$ represents alkyl having 3–12 carbon atoms or phenyl, and $R_3$ and $R_4$ each represents lower alkyl, which comprises reacting a carboxylic acid ester of the formula II $$R_1 - C \equiv C - CO - O - O R_2 \quad \text{(II)}$$

wherein $R_2$ represents lower alkyl and $R_1$ has the meaning given under formula IV with approximately an equimolar amount of 3-oxoglutaric acid of the formula III $$R_3-O-CO-CH_2-CO-CH_2-CO-O-R_4 \quad \text{(III)}$$

wherein
$R_3$ and $R_4$ have the meaning given under formula IV, in the presence of approximately an equimolar amount of an alkali metal hydride in an inert organic solvent at between 0° and room temperature and, adding approximately an 1- to 1.5-fold molar amount of the alkali metal hydride, reacting the whole at ca. 80° C to 140° C, and separating the dihydroxyisophthalic acid ester of the formula IV from the resulting crude reaction product.

8. Process according to claim 7, wherein the employed carboxylic acid ester of the formula II is one in which $R_1$ represents pentyl or phenyl, and $R_2$ represents lower alkyl.

9. Process according to claim 7, wherein the addition of approximately an 1- to 1.5-fold molar amount of the alkali metal hydride is made after 5 to 90 minutes of reaction time.

* * * * *